United States Patent
Jones et al.

[11] Patent Number: 5,879,387
[45] Date of Patent: Mar. 9, 1999

[54] PROSTHETIC BEARING ELEMENT AND METHOD OF MANUFACTURE

[75] Inventors: Thomas E. Jones, Ardlahan Kildimo, Ireland; Nigel G. Smith, Wokingham, England

[73] Assignee: Howmedica International Inc., Shannon, Ireland

[21] Appl. No.: 932,573

[22] Filed: Sep. 19, 1997

Related U.S. Application Data

[63] Continuation of Ser. No. 516,734, Aug. 18, 1995, abandoned.

[30] Foreign Application Priority Data

Aug. 25, 1994 [GB] United Kingdom ............... 9417288

[51] Int. Cl.$^6$ ........................................ A61F 2/30
[52] U.S. Cl. ........................................ 623/18; 623/20
[58] Field of Search ................. 623/18, 20, 22, 623/23

[56] References Cited

U.S. PATENT DOCUMENTS

| | | | |
|---|---|---|---|
| 4,267,608 | 5/1981 | Bora, Jr. ................................ | 403/111 |
| 4,778,472 | 10/1988 | Homsy et al. ......................... | 623/18 |
| 4,911,718 | 3/1990 | Lee et al. .............................. | 623/17 |
| 5,047,054 | 9/1991 | Vijayan et al. ....................... | 623/16 |
| 5,067,964 | 11/1991 | Richmond et al. .................... | 623/18 |
| 5,092,896 | 3/1992 | Meuli et al. ........................... | 623/21 |
| 5,201,881 | 4/1993 | Evans .................................... | 623/20 |
| 5,344,459 | 9/1994 | Swartz .................................. | 623/18 |
| 5,609,646 | 3/1997 | Field et al. ............................ | 623/22 |
| 5,645,594 | 7/1997 | Devanathan et al. ................. | 623/22 |

FOREIGN PATENT DOCUMENTS

| | | |
|---|---|---|
| 203719 A | 12/1986 | European Pat. Off. . |
| 297789 A | 1/1989 | European Pat. Off. . |
| 2126096 | 3/1984 | United Kingdom . |
| WO 9011060 | 10/1990 | WIPO . |

*Primary Examiner*—Michael J. Milano
*Assistant Examiner*—Bruce E. Snow
*Attorney, Agent, or Firm*—Peter C. Richardson; Lawrence C. Akers; Raymond W. Augustin

[57] ABSTRACT

A prosthetic bearing element comprises a backing which supports a bearing liner having a bearing surface. The backing is made from a "hard" polymeric material having a minimum hardness value of 55 N/mm$^2$ and the bearing liner is made from a "soft" elastomeric polyurethane material having a hardness value of 3.0 to 9.0 N/mm$^2$.

10 Claims, 5 Drawing Sheets

PROSTHETIC BEARING ELEMENT AND METHOD OF MANUFACTURE

This is a continuation of application Ser. No. 08/516,734, filed on Aug. 18, 1995, now abandoned.

BACKGROUND OF THE INVENTION

1. Field of the Invention

This invention relates to a prosthetic bearing element and to a process for making such an element. More particularly it relates to the use of a polyurethane bearing component which results in the formation of a fluid film bearing between the metal joint part and the bearing surface.

2. Description of the Prior Art

Improved wear of bearing surfaces such as polyethylene acetabular components in hips, tibial component in knees, and other prosthetic bearing inserts is a major goal for the success of artificial joints. Orthopaedic devices for joint construction and reconstruction can comprise polyethylene bearings on metal, ceramic on polyethylene, and metal on metal. Polyethylene bearings are often held in a metal shell, for example in hip prosthesis or a tibial tray in knee prosthetics. Conventionally bearing liners made from ultra-high molecular weight polyethylene are fixed via a snap fit into the metal backing.

The possible use of elastomers in bearings to provide fluid film lubrication at low velocity, low viscosity lubricant has been published in laboratory studies which show that such "soft" bearings provide lower coefficient of friction compared with standard polyethylene versus metal bearings. Such a material is polyurethane. This fluid film bearing mimics the natural lubrication of the joint where synovial fluid lubricates the bone cartilage interface. Because of the fluid film lubrication, it is less likely that the two bearings touch during use and thus wear is lower.

It is however difficult to apply this concept to artificial joints for a number of reasons. One difficulty lies in selecting a suitable elastomer such as polyurethane which will not be degraded or rejected by the human body so care must be taken in selecting the polyurethane materials used. As mentioned above, polyethylene bearings are usually held by physical means in, for example, a metal shell but it is not possible to use this approach with polyurethane because as its stiffness is so much lower than the metal it would be possible under load to be extruded from the metal shell or easily moved relative to the shell causing damage. Moreover, the lower stiffness of the bearing leads to greater differential interface stain between the shell and the liner.

Because of the above difficulties the applicants have tried several different approaches. Initially, for ease of use and conventional appearance, it was attempted to bond a polyurethane liner into a polyethylene backing, similar to pre-existing polyethylene components. This could then be held in a metal shell or cemented depending on the surgeon's preference.

SUMMARY OF THE INVENTION

It is an object of the present invention to provide a prosthetic bearing element which uses an elastomeric polyurethane bearing material and to a method of manufacturing such a bearing element which overcomes some of the difficulties referred to above.

According to the present invention a prosthetic bearing element comprises a backing which supports a bearing liner having a bearing surface. The backing is made from a "hard" or "rigid" polymeric material having minimum hardness value of 65 N/mm$^2$ and the bearing liner being made from a "soft" or "compliant" elastomeric polyurethane material having a hardness value of 3.0 to 9.0 N/mm$^2$.

It has been found that bearing elements of this type can be made by a molding process and the unexpected result is that when the elastomeric material is applied onto a "hard" or "rigid" polyurethane backing the stability of the interface appears to be better than that predicted by simple mechanical fit. It is not clear whether there is some form of chemical bond and what precisely causes the excellent adhesion between the two materials. It is possible that an interpenetrating network of the "soft" elastomeric polyurethane into the hard polymer results.

Preferably therefore the liner is bonded to the backing and the backing itself can also be made from a range of rigid polyurethanes. Suitable polyurethane formulations include those based upon macroglycols formed from polyether glycols i.e. polytetramethylene ether glycol, or polyhexamethylene ether glycol, or polyoctamethylene ether glycol or polydecamethylene ether glycol, or polyester based glycols i.e. polyhexamethylene adipate glycol. The aforementioned macroglycols which are suited to reaction with suitable diisocyanates i.e. 4,4'-methylene bisphenyl diisocyanate, or 4,4'-methylene biscyclohexane diisocyanate, or 2,4-toluene diisocyanate and reacted further with chain extenders i.e. 1,4-butanediol, 1,6-hexanediol, ethylene diamine, 1,4-cyclohexane diamine. Polyurethane of different compositions can be synthesized by those skilled in the art from a range of these materials in many combinations.

A suitable material is COROTHANE polyurethane 75D, a rigid segmented linear polyurethane polymer comprising of a polycarbonate based macroglycol, poly (1,6-hexyl 1,2-ethyl carbonate) diol reacted with 4,4'-methylene bisphenyl diisocyanate and chain extended using 1,4-butanediol. The hardness being determined by the ratio of hard segments (formed by the isocyanate and chain extended domains) to the soft segments (formed by the macroglycol portion of the polymer chain) (COROTHANE polyurethane is a Registered Trademark of Corvita Corporation), or carbon fiber reinforced polybutyleneterphthlate (CFR-PBT). Another alternative material which can be used is carbon fiber reinforced polyetheretherketone (CFR-PEEK).

In a preferred construction the bearing liner is made from COROTHANE polyurethane 80A.

A soft segmented linear polyurethane polymer comprising of a polycarbonate based macroglycol, poly (1,6-hexyl 1,2-ethel carbonate) diol reacted with 4,4'-methylene bishenyl disocyanate and chain extending using 1,4-butanediol. If desired two or more bearing liners can be provided on the backing thus, the bearing element can be used in this manner in the form of a meniscal bearing for use in a knee prosthesis.

Suitable polyurethane formulations for the backing include those based upon macroglycols formed from polyether glycols i.e., polytetramethylene ether glycol, polyhexamethylene ether glycol or polyoctamethylene ether glycol or polydecamethylene ether glycol, or polyester based glycols i.e., polyhexamethylene adipate glycol. The aforementioned macroglycols which are suited to reaction with suitable diisocyanates i.e., 4,4'-methylene bisphenyl diisocyanate, or 4,4'-methylene biscyclohexane diisocyanate, or 2,4-toluene diisocyanate and reacted further with chain extenders i.e., 1,4-butanediol, 1,6-hexanediol, ethylene diamine, 1,4-cyclohexane diamine. Polyurethane of different compositions can be synthesized by those skilled in the art from a range of these materials in many combination. Other backing materials can be a rigid segmented linear polyurethane polymer comprising a polycarbonate based macroglycol, poly (1,6-hexyl 1,2-ethyl carbonate) diol reacted with 4,4'-methylene bisphenyl diisocyanate and chain extended using 1,4-butanediol. The hardness being determined by the ration of hard segments (formed by the isocyanate and chain extender domains) to the soft segments (formed by the macroglycol portion of the polymer chain). The liner can be a soft segmented linear polyurethane polymer comprising of a polycarbonate based macroglycol, poly (1,6-hexyl 1,2-ethyl carbonate) diol reacted with 4,4'-methylene bisphenyl diisocyanate and chain extended using 1,4-butanediol.

The invention can be applied to an acetabular cup or any other suitable prosthetic bearing. If desired two or more bearing liners can be provided on the backing thus, the bearing element can be used in this manner in the form of a meniscal bearing for use in a knee prosthesis. The invention also includes a prosthetic implant incorporating a bearing element as set forth above.

A process, according to the invention, for making a prosthetic bearing element as set forth above can include a two state molding process in which the backing or liner is molded first and then the appropriate liner or backing is molded onto it. Thus, the two-parts are molded consecutively rather than simultaneously.

Studies undertaken by scanning electron microscopy (SEM), dynamic contact angle (DCA) and fourier transform infra-red spectroscopy (FTIR) have been undertaken to examine the interfacial region to determine the structural changes that occur.

The introduction of barium sulphate ($BaSO_4$) at 5% m/m into the elastomer, COROTHANE polyurethane 80A, have shown the interface zone to be discrete at 2–5 micron and reproducible. In addition the structural composition of the COROTHANE polyurethane 80A and COROTHANE polyurethane 75D polyetherurethanes has been examined by recording their spectra over a series of sectors (5 mm×220 $\mu$m) across a section through the interface region.

This FTIR technique allows the ratio of hard to soft segments in the linear polyetherurethane's to be quantified. The results show that the structure has been modified in the COROTHANE polyurethane 75D to gradually change the composition from the interface zone to approximately 50 microns into the bulk as a result of the second molding operation using COROTHANE polyurethane 80A. It is this structural modification that occurs via the over molding of the "rigid" shell material (COROTHANE polyurethane 75D) with the elastomer (COROTHANE polyurethane 80A) that appears to provide the adhesion between the two linear polyetherurethanes.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

In the drawings, wherein similar reference characters denote similar elements throughout the several views.

DESCRIPTION OF THE PREFERRED EMBODIMENT

Figure 1:
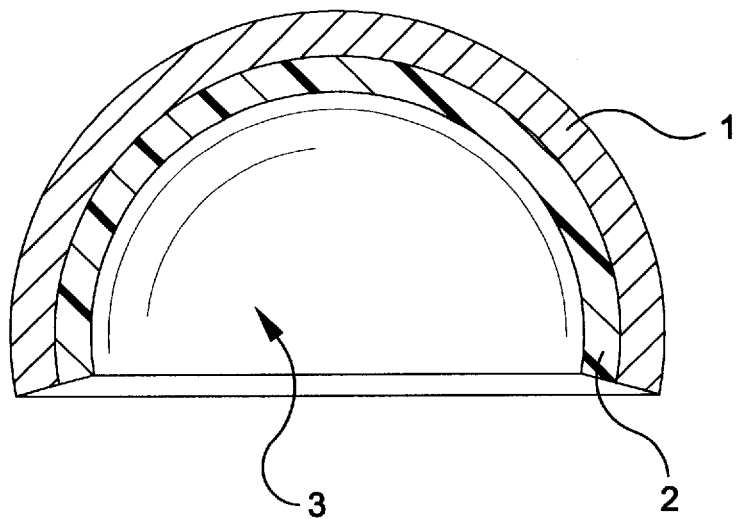
FIG. 1 is a cross-sectional view through a typical acetabular cup incorporating the invention.

FIG. 1 is a cross-section through a prosthetic hip cup according to the invention and which comprises an outer backing 1 which is made from a "hard" or "rigid" polymeric material having a minimum hardness value of about 65N/$mm^2$. The backing 1 supports a bearing liner 2 made from a "soft" elastomeric polyurethane material having a hardness value of about 3.0 to 9.0N/$mm^2$ and a range of thickness of 1 to 5 mm.

The terms "hard", "rigid" and "soft" are used throughout the specification to indicate the relative properties of the material from which the backing and the liner are made.

The bearing surface of the cup shown in FIG. 1 is indicated by reference numeral 3.

Figure 2:
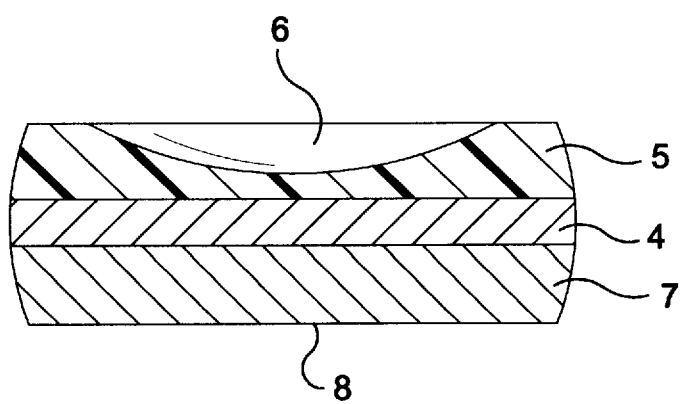
FIG. 2 is a cross-sectional view through a meniscal bearing for use in knee prosthesis incorporating the invention.

FIG. 2 shows as meniscal bearing for use with the tibial tray of a knee prosthesis. The bearing comprises a backing 4 made of a "rigid" polymeric material having a minimum hardness value of about 65N/$mm^2$ and an upper liner 5 having a bearing surface 6 and a lower liner 7 having a bearing surface 8. The liners 5 and 7 are made from a "soft" or "compliant" elastomeric polyurethane material having a hardness value of about 3.0 to 9.0 N/$mm^2$ and a range of thickness of 1 to 5 mm.

Figure 3:
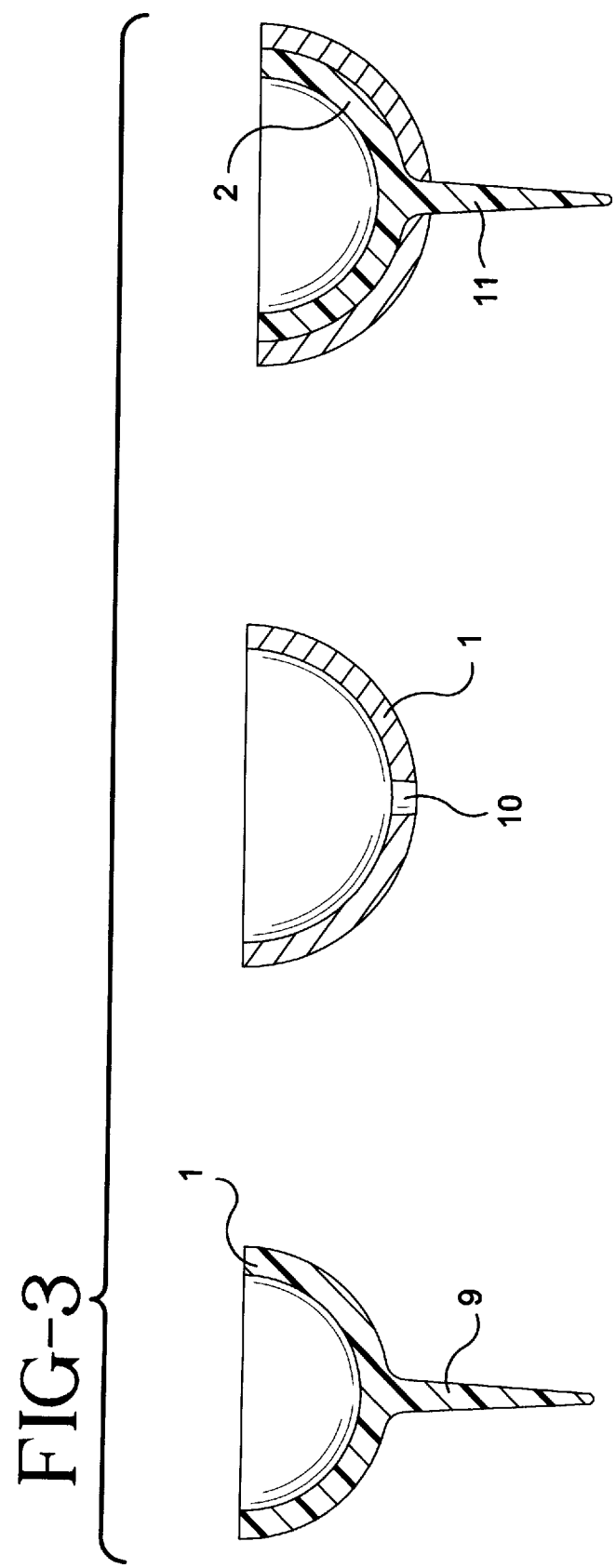
FIG. 3 diagrammatically illustrates three stages of molding a prosthetic bearing element in which the backing is molded first in a two-part process.

FIG. 3 shows diagrammatically a process for molding a bearing element of the kind shown in FIG. 1. Backing 1 is molded first in a suitable injection mold and which leaves a sprue 9. The backing is now taken out of the mold and sprue 9 removed. A hole 10 is drilled through the backing 1 which is then replaced in the mold and liner 2 is molded by utilizing hole 10. The sprue left by liner 2 is indicated by reference numeral 11. This is then removed to provide the completed bearing.

Figure 4:
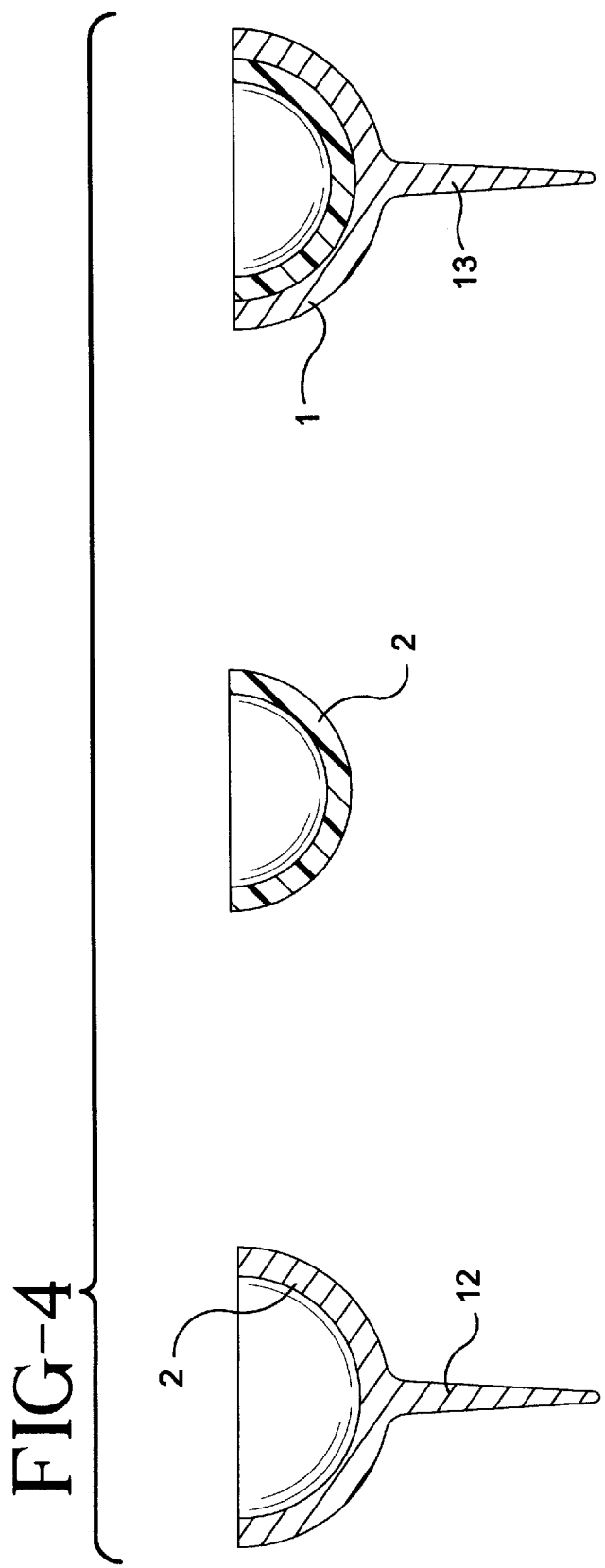
FIG. 4 is a diagrammatic illustration showing the stages of molding a similar bearing element to that shown in FIG. 1 molding the bearing liner first in a two-part process.

FIG. 4 shows an alternative way of molding the bearing element and in this arrangement liner 2 is molded first and there is a sprue 12. Liner 2 is taken out of the mold, sprue 12 removed and the liner replaced in the mold where backing 1 is molded onto it. This again produces a sprue 13 which is subsequently removed to provide the finished bearing element.

Figure 5:
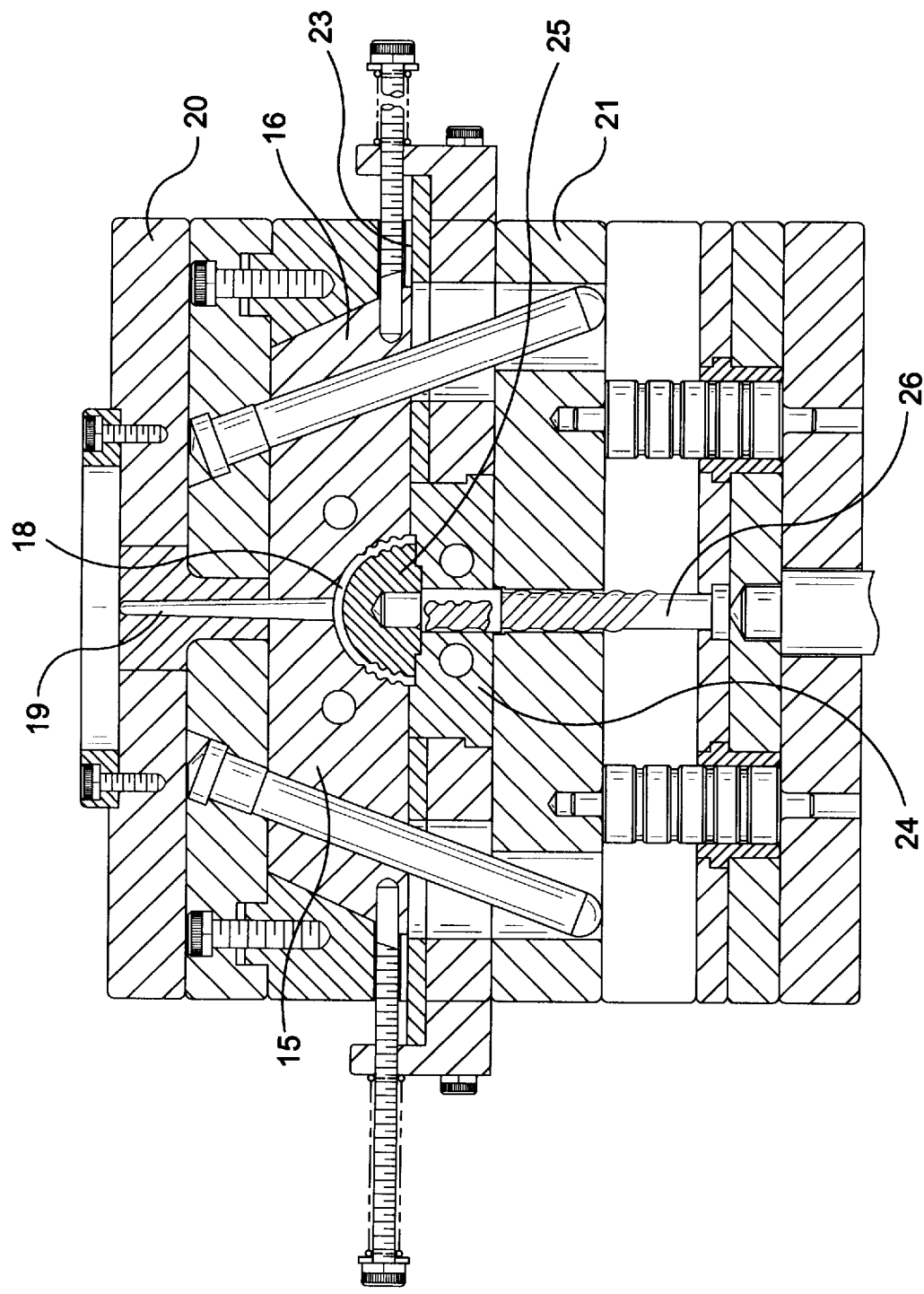
FIG. 5 is a cross-sectional view through an injection mold for use in the he process according to the invention; and, FIG. 6 is a diagrammatic side elevation of a typical injection molding machine showing various areas of the injection molding barrel.

FIG. 5 shows a suitable injection mold which can be used in the process. The general construction of the mold will be familiar to those skilled in the art and will not therefore be described in detail. The mold includes a pair of backing plates 15, 16 which together form a mold cavity 18 which can be fed from an injection molding machine through an opening 19.

The mold is in two general parts, 20 and 21, and can be opened along a line 23. The part 21 of the mold carries a mounting 24 on which can be secured a male molding element 25. This is secured by a bolt 26. In order to mold bearing elements of different sizes a number of backing plates 15, 16 and mold elements 25 are provided.

In order to mold in the process shown in FIG. 3, that is by molding backing element 1 first, a suitably dimensioned molded element 25 is secured in place together with appropriate backing plates 15 and 26 and the mold presses operated to inject material though the opening 19 into molding space 18 to form a backing of the kind shown at the left hand side of FIG. 3. The mold is now opened along the line 23 and the molded element 25 together with backing 1 is detached. The backing, as molded, is then removed from the mold element 25 and sprue 9 which has formed in the opening 19 is removed. A hole 10 is now drilled in the backing and the backing is replaced in the mold with a different mold element 25 of smaller dimensions so that there is now a mold opening between backing 1 and the surface of mold element 25. Molding material is now injected through opening 19 and hole 10 in backing 1 so that it fills the space between the backing and mold element 25. With molding completed the mold is again split, the molded bearing element separated from molding element 25 and sprue 11 which has formed in opening 19 removed.

In order to mold according to the process shown in FIG. 4 with the same apparatus the process is carried out by using appropriately sized backing plates 15 and 16 and mold element 25 to produce the inner lining. With sprue 12 removed the lining is replaced in the mold but this time with different backing plates 15, 16 which provide a cavity between liner 2 and the edges of cavity 18. The backing is now molded in place, is removed in a manner described above and sprue 13 removed.

It will be appreciated that the above is a relatively simple way of molding according to the process and other molding techniques known in the art can be employed.

Using the above type of apparatus shown in FIGS. 5 and 5A the following combinations of materials have been molded and have produced satisfactory examples.

Figure 6:
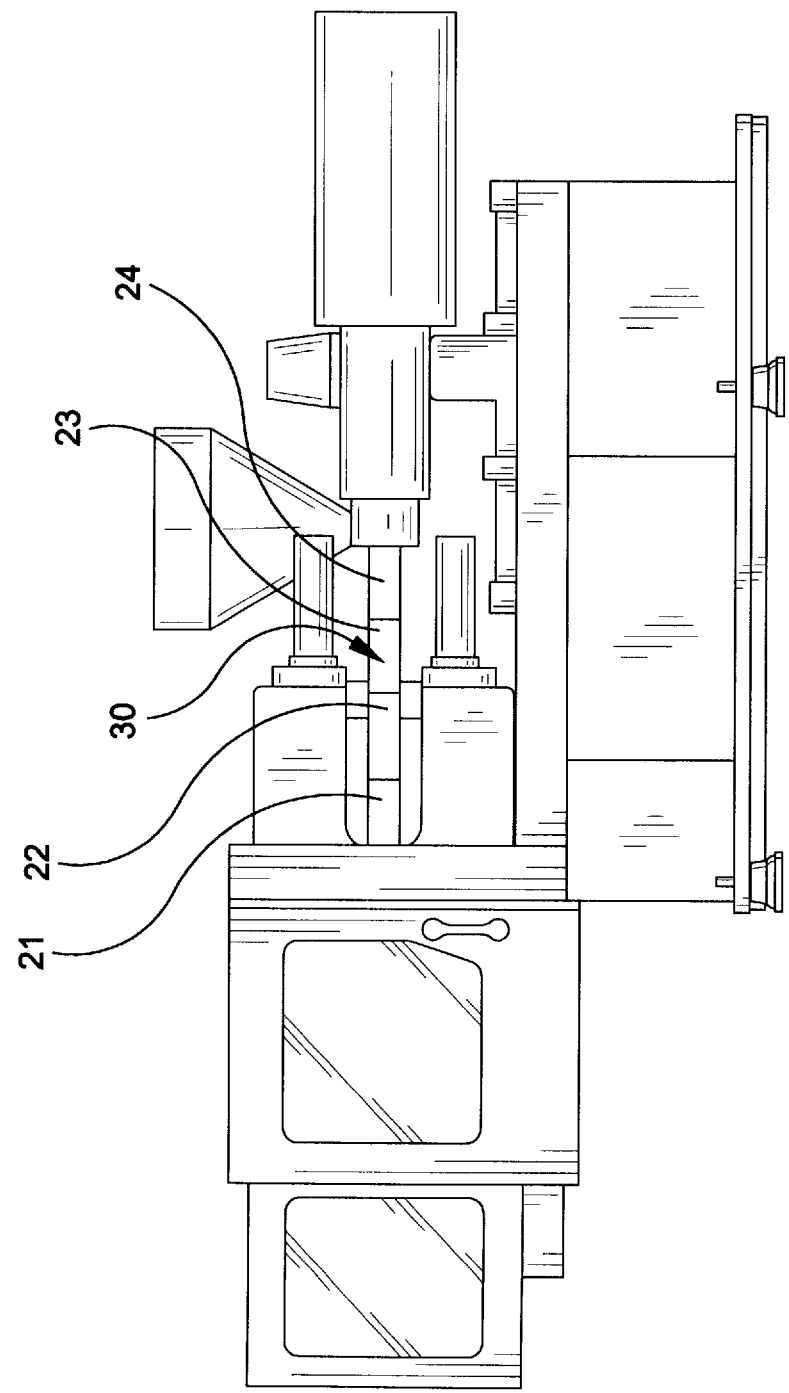

FIG. 6 shows a typical commercial ejection molding machine and in which the injection molding barrel is indicated by reference numeral 30. The various areas along the extending length of the barrel 30 are indicated by reference numerals Z1, Z2, Z3 and Z4. Reference to the temperatures in the barrel are shown in the following examples.

The screen speed and injection speed referred to are dimensionless covering an analogue range from 1.0 to 5.0. They are varied from time to time dependent upon cavity volume or melt viscosity.

EXAMPLE 1
Molding CSIRO onto COROTHANE polyurethane C75D
CSIRO 85A (lot no. 1267-1193) dried.

| Injection conditions | |
|---|---|
| Times: | Inj (15 sec); Holding (20 sec) |
| Pressure: | Injection (50 bar), Hold (25 bar) |
| Cooling mold: | 10 C. (20 sec) |
| Screw speed: | 3.0 |
| Injection Speed: | 4.0 |
| Injection temp: | 205° C. (Z1) |
| barrel: | 201° C. (Z2) |
| barrel: | 201° C. (Z3) |
| barrel: | 191° C. (Z4) |

Peel test samples using ptfe tape as crack indicator. Samples 40–45 prepared using he earlier produced C75 pieces No. 40–55

EXAMPLE 2
Molding TECOTHANE onto COROTHANE polyurethane C75D TECOTHANE 93A dried.

| Injection Conditions | |
|---|---|
| Times: | Inj (15 sec); Holding (20 sec); cooling (20 sec) |
| Pressure: | Injection (50 bar), Hold (25 bar) |
| Cooling mold: | 10 C. (20 sec) |
| Screw speed: | 3.0 |
| Injection speed: | 4.0 |
| Injection temp: | 205° C. (Z1) |
| barrel: | 201° C. (Z2) |
| barrel: | 200° C. (Z3) |
| barrel: | 191° C. (Z4) |

Peel test samples using ptfe tape as crack indicator. No. 56 to 70.

EXAMPLE 3
Molding Choroflex onto COROTHANE polyurethane C75D Choroflex AL80A (lot no. CF 137) dried.

| Injection conditions | |
|---|---|
| Times: | Inj (15 sec); Holding (20 sec) |
| Pressure: | Injection (65 bar) Hold (30 bar) |
| Cooling mold: | 10° C. (sec) |
| Injection speed: | 5.0 |
| Injection speed: | 3.0 |
| Injection temp: | 205° C. (Z1) |
| barrel: | 201° C. (Z2) |
| barrel: | 201° C. (Z3) |
| barrel: | 191° C. (Z4) |

Peel test samples using ptfe tape as crack indicator. No. 71 to 87.

EXAMPLE 4
Molding Pellethane onto COROTHANE polyurethane C75D Pellethane 80A (lot no. 2363) dried

| Injection conditions | |
|---|---|
| Times: | Inj (15 sec); (Holding (20 sec) |
| Pressure: | Injection (50 bar), Hold (25 bar) |
| Cooling mold: | 10° C. (20 sec) |
| Screw speed: | 3.0 |
| Injection speed: | 5.0 |
| Injection temp: | 205° C. (Z1) |
| barrel: | 201° C. (Z2) |
| barrel: | 191° C. (Z3) |
| barrel: | 160° C. (Z4) |

Peel test samples using ptfe tape as crack indicator. No. 88 to 102

EXAMPLE 5
Molding COROTHANE polyurethane 55D onto COROTHANE polyurethane C75D COROTHANE polyurethane 55D (lot no. PEA0072) dried

| Injection conditions | |
|---|---|
| Times: | Inj (15 sec); Holding (20 sec) |
| Pressure: | Injection (50 bar), Hold (25 bar) |
| Cooling mold: | 10° C. (20 sec) |
| Screw speed: | 3.0 |

-continued

| Injection conditions | |
|---|---|
| Injection speed: | 5.0 |
| Injection temp: | 222° C. (Z1) |
| barrel: | 218° C. (Z2) |
| barrel: | 209° C. (Z3) |
| barrel: | 190° C. (Z4) |

Peel test samples using ptfe tape as crack indicator. No. 103 to 116

EXAMPLE 6

Molding COROTHANE polyurethane 80A onto TECOTHANE C75D

COROTHANE polyurethane 80A (lot no. PEA00038) dried.

| Injection conditions | |
|---|---|
| Times: | Inj (15 sec); Holding (20 sec) |
| Pressure: | Injection (50 bar), Hold (25 bar) |
| Cooling mold: | 10° C. (20 sec) |
| Screw speed: | 3.0 |
| Injection speed: | 5.0 |
| Injection temp: | 216° C. (Z1) |
| barrel: | 216° C. (Z2) |
| barrel: | 205° C. (Z3) |
| barrel: | 160° C. (Z4) |

Peel test samples using ptfe tape as crack indicator. No. 117 to 141

EXAMPLE 7

Further backing pieces were molded from COROTHANE polyurethane 75D as follows.

Molding of COROTHANE polyurethane 75D test pieces

| Injection conditions | |
|---|---|
| Times: | Inj (15 sec); Holding (20 sec) |
| Pressure: | Injection (50 bar), Hold (25 bar) |
| Cooling mold: | Ambient (20 sec) |
| Screw speed: | 3.0 |
| Injection speed: | 5.0 |
| Injection temp | 229° C. (Z1) |
| barrel: | 223° C. (Z2) |
| barrel: | 211° C. (Z3) |
| barrel: | 200° C. (Z4) |

Such backing pieces were ready for use with suitable liners.

EXAMPLE 8

Liners themselves were also made individually from COROTHANE polyurethane 80A under the following conditions.

COROTHANE polyurethane 80A dried

| Injection conditions | |
|---|---|
| Times: | Inj (15 sec); Holding (20 sec) |
| Pressure: | Injection (59 bar), Hold (25 bar) |
| Cooling mold: | 10° C. (20 sec) |
| Screw speed: | 3.0 |
| Injection speed: | 5.0 |
| Injection temp: | 208° C. (Z1) |

-continued

| Injection conditions | |
|---|---|
| barrel: | 203° C. (Z2) |
| barrel: | 191° C. (Z3) |
| barrel: | 160° C. (Z4) |

These liners were suitable for use with backing of suitable material.

EXAMPLE 9

Further "hard" backing materials can be used for example what are usually referred to as Composites, that is a synthetic resin material with, for example, a fibre reinforcement. Example A set out below was the use of carbon fibre reinforced polybutyleneterphthlate (CFR-PBT).

| Times: | Inj (4 sec), Hold (4 sec) |
|---|---|
| Pressure: | Inj (40 bar), Hold (10 bar) |
| Temp: | Injection 240° C. |
| Mold: | 80° C. |
| Injection speed: | 3 |

Another alternative material which was successfully injected was polyetheretherketone (CFR-PEEK) as follows.

| Times: | Inj (4 sec), Hold (4 sec) |
|---|---|
| Pressure: | Inj (40 bar), Hold (12 bar) |
| Temp: | Injection 390° C. |
| Mold: | 180° C. |
| Injection speed: | 3 |

These materials were successfully used as backings, again with, for example, with COROTHANE polyurethane 80.

Experiments were carried out to establish the relative hardnesses of different materials and hardness testing of the various elastomers was undertaken investigating the effect of irradiation on the hardness of PEU elastomers using BS 2782; Pt 3 Method 365D (Test load 49N—Shore 80–93A; Test load 358N—Shore 75D).

The results of the hardness examination are shown below.

| Material | Hardness (Nmm$^{-2}$) |
|---|---|
| COROTHANE polyurethane 80A | 5.380 (°0.146) |
| Tecoflex EG93A | 4.468 (°0.050) |
| TECOTHANE TT1080A | 5.191 (°0.041) |
| Chronoflex AL80A | 3.977 (°0.030) |
| CSIRO 85A | 7.894 (°0.147) |
| COROTHANE polyurethane 75D | 89.40 (°2.31) |
| COROTHANE polyurethane 55D | 65 |
| TECOTHANE 75D | 84.5 (°2.59) |

°denotes standard deviation

As will be seen the differences between "hard" and "soft" are apparent.

A peel test was performed to assess the bond between the rigid backing and the flexible inner layer. The test used is a standard test in which a 3 mm thick flexible layer is bonded to an 8 mm thick rigid backing with the last 35 mm unbonded (or bonded and then debonded). The flexible layer is gripped and pulled at a peel angel of 60° in a Lloyd R6000 Universal testing machine. The force required to peel the layers apart is recorded as the peeling continues for about 50 mm.

The table below shows the results of this test where N is the mean peel force, the Strain Energy is in the area under the force vs. peel distance curve and the adhesive Fracture Energy is the energy released per unit of new surface created on separating the interface.

| Backing Shell | Bearing Elastomer | Peel force (N) | Strain Energy (Kjm$^{-3}$) | Fracture Energy (JM$^{-2}$) |
|---|---|---|---|---|
| UHMWPE | COROTHANE polyurethane 80A | 10 | n.d. | n.d. |
| UHMWPE | Tecoflex | 1.3 | n.d. | n.d. |
| UHMWPE *pAA | Tecoflex | 2.9 | n.d. | n.d. |
| UHMWPE *pHEMA | Tecoflex | 2.9 | n.d. | n.d. |
| UHMWPE //NH$_3$ | COROTHANE polyurethane 80A | 10 | 0.96 | 95 |
| UHMWPE //allylamine | COROTHANE polyurethane 80A | 4.22 | 0.148 | 39.5 |
| COROTHANE polyurethane 75D | COROTHANE polyurethane 80A | 407 | 6,478 | 20,010 |
| TECOTHANE 75D | COROTHANE polyurethane 80A | 523 | n.d. | n.d. |
| COROTHANE polyurethane 75D | CSIRO 85A | 315 | n.d. | n.d. |
| COROTHANE polyurethane 75D | COROTHANE polyurethane 55D | 502 | n.d. | n.d. |
| COROTHANE polyurethane 75D | Chronoflex AL80A | 403 | n.d. | n.d. |
| COROTHANE polyurethane 75D | Pellethane 80A | 542 | n.d. | n.d. | n.d. denotes not determined
* denotes photochemical grafting
// denotes functionalization of PE by plasma modification
NH$_3$ (ammonia plasma)
Allylamine (allylamine to quench radicals by an oxygen plasma)
PEI (polyethyleneimine to quench radicals generated by an oxygen plasma)

It will be seen that the peel force required for the first six combinations of materials is very low but immediately "hard" and "soft" materials are applied together the peel force required rises dramatically.

This ability to resist separation is utilized in the preparation of the bearing elements of the kind set forth in the present invention.

We claim:

1. A prosthetic bearing element for sliding engagement with a joint surface comprising a backing bonded by molding to at least one bearing liner having a bearing surface for engaging said joint surface, said backing made from a rigid polymeric material having a minimum hardness value of 65 N/mm$^2$ and said bearing liner being molded onto said backing from a softer elastomeric polyurethane material having a hardness value of 3.0 to 9.0 N/mm$^2$, wherein the prosthetic bearing element includes two bearing liners bonded onto said backing.

2. The prosthetic bearing element as claimed in claim 1 in which said backing is made from polyurethane.

3. The prosthetic bearing element as claimed in claim 1 in which said backing is made from carbon fiber reinforced polybutyleneterphthlate.

4. The prosthetic bearing element as claimed in claim 1 in which said backing material is made from polyetheretherketone.

5. The prosthetic bearing element as claimed in claim 1 in which said backing material is made from polymethylmethacrylate.

6. A prosthetic bearing element for sliding engagement with a joint surface comprising a backing bonded by molding to at least one bearing liner having a bearing surface for engaging said joint surface, said backing made from a rigid polymeric material having a minimum hardness value of 65 N/mm$^2$ and said bearing liner being molded onto said backing from a softer elastomeric polyurethane material having a hardness value of 3.0 to 9.0 N/mm$^2$, wherein the prosthetic bearing element is shaped to match the natural condyles to form a bearing insert for use in a knee prosthesis.

7. The prosthetic bearing element as claimed in claim 6 in which said backing is made from polyurethane.

8. The prosthetic bearing element as claimed in claim 6 in which said backing is made from polybutyleneterphthlate.

9. The prosthetic bearing element as claimed in claim 6 in which said backing is made from polyetheretherketone.

10. The prosthetic bearing element as claimed in claim 6 in which said backing is made from polymethylmethacrylate.

* * * * *

UNITED STATES PATENT AND TRADEMARK OFFICE
CERTIFICATE OF CORRECTION

PATENT NO. : 5,879,387
DATED : March 9, 1999
INVENTOR(S) : Jones et al.

It is certified that error appears in the above-identified patent and that said Letters Patent is hereby corrected as shown below:

Column 3, line 42, "polyetherurethane's" should read -- polyetherurethanes --.
Column 4, line 8, cancel the word "he".
Column 4, line 29, "as" should read -- a --.
Column 5, line 20, after "19", insert -- is --.
Column 5, line 39, cancel the word "and".
Column 5, line 66, "he" should read -- the --.
Column 6, line 27, "(sec)" should read -- (20sec) --.
Column 8, line 34, delete the word "with" (second occurrence).
Column 9, line 33, "immediately" should read -- when for immediately --.

Signed and Sealed this

Second Day of January, 2001

*Attest:*

*Attesting Officer*

Q. TODD DICKINSON

*Commissioner of Patents and Trademarks*